United States Patent [19]

Oroszlan et al.

[11] Patent Number: 5,354,683
[45] Date of Patent: Oct. 11, 1994

[54] HUMAN IMMUNODEFICIENCY VIRUS SPECIFIC PROTEOLYTIC ENZYME AND A METHOD FOR ITS SYNTHESIS AND RENATURATION

[75] Inventors: Stephen Oroszlan, Potomac; Terry D. Copeland, Frederick, both of Md.

[73] Assignee: The United States of America as represented by the Department of Health and Human Services, Washington, D.C.

[21] Appl. No.: 100,703

[22] Filed: Jul. 30, 1993

Related U.S. Application Data

[63] Continuation of Ser. No. 201,654, Jun. 1, 1988, abandoned, which is a continuation-in-part of Ser. No. 174,473, Mar. 28, 1988, abandoned, which is a continuation of Ser. No. 107,880, Oct. 9, 1987, abandoned, which is a continuation of Ser. No. 57,183, Jun. 1, 1987, Pat. No. 5,252,477.

[51] Int. Cl.[5] ........................ C12N 9/50; C12N 7/04
[52] U.S. Cl. ................................ 435/219; 435/235.1; 435/236

[58] Field of Search ............... 435/212, 219, 235.1, 435/236, 948; 935/3, 5

[56] References Cited

U.S. PATENT DOCUMENTS

5,252,477 10/1993 Oroszlan et al. .................... 435/219

OTHER PUBLICATIONS

Pearl, L. H., et al. (1987) Nature 328, 482.
Guyader, M., et al. (1987) Nature 326, 662–669.
Pearl, L. H., et al. (1987) Nature 329, 351–354.

Primary Examiner—Charles L. Patterson, Jr.
Attorney, Agent, or Firm—Knobbe, Martens, Olson & Bear

[57] ABSTRACT

HIV protease necessary for the natural synthesis of HIV has been identified and sequenced. This antibody cross reacts with the protease of HIV-2. In addition, a method for producing synthetic HIV-1 and HIV-2 protease having the correct stereospecific conformation and specific HIV proteolytic activity has been achieved. Assays for the synthetic proteases using synthetic peptide substrates have been developed.

3 Claims, 7 Drawing Sheets

CONSERVED SEQUENCES OF RETROVIRAL PROTEASES

CLEAVAGE SITE SPECIFICITY

| | 1 | 17 | 30 | 56 | 87 | 92 | 125 | |
|---|---|---|---|---|---|---|---|---|
| M-MULV | \| | RIT | LVDTGA | GATG | DC | LLGRD | \| | a |
| AKR | | ... | ...... | .... | .. | ..... | | a |
| FELV | | ... | ...... | .... | .. | ..... | | a |
| BAEV | | ... | ...... | .... | .. | ..... | | a |
| HTLV-I,-II | | ... | ...... | .... | S· | ..... | | a |
| BLV | | SGP | ...... | GAGG | KI | ..... | | b |
| VISNA | | IKV | ...... | IGGI | SP | ..... | | c |
| EIAV | | IND | ...... | TGII | VA | ..... | | d |
| HTLV-III | | LVT | ...... | GGTI | VN | ..... | | e |

| | | | | | |
|---|---|---|---|---|---|
| a | S | S | L | Y | ·P |
| b | P | A | I | L | ·P |
| c | R | E | V | Y | ·P |
| d | S | E | E | Y | ·P |
| e | S | Q | N | Y | ·P |
| | P4 | P3 | P2 | P1 | |

FIGURE 1

```
HIV-1BH10      ProGlnIleThrLeuTrpGln                        7
HIV-2ROD                PheSer        Lys

ArgProLeuValThrIleLysIleGlyGlyGlnLeuLysGluAla              22
    Val       AlaTyr  Glu       ProVal  Val

LeuLeuAspThrGlyAlaAspAspThrValLeuGluGluMetSer              37
                      SerIleValAlaGlyIleGlu

LeuProGlyArgTrpLysProLysMetIleGlyGlyIleGlyGly              52
    GlyAsnAsnTyrSer       IleVal

PheIleLysValArgGlnTyrAspGlnIleLeuIleGluIleCys              67
    AsnThrLysGlu    LysAsnValGlu        ValLeu

GlyHisLysAlaIleGlyThrValLeuValGlyProThrProVal              82
AsnLys   ValArgAla   IleMetThr    Asp        Ile

AsnIleIleGlyArgAsnLeuLeuThrGlnIleGlyCysThrLeu              97
    Phe        Ile      AlaLeu     MetSer

AsnPhe.
    Leu
```

*Fig. 2*

```
                                                                    GAG p15  1
BH10   GGAGCCGATAGACAAGGAACTGTATCCTTTAACTTCCCTCAGATCACTCTTTGGCAACGACCCCTGTCACAATA    1871
       GlyProIleAspLysGluLeuTyrProLeuThrSerLeuArgSerLeuPheGlyAsnAspProSerSerGln
       GlyAlaAspArgGlnGlyThrValSerPheAsnPheProGlnIleThrLeuTrpGlnArgProLeuValThrIle
                                                          ↳PR

BH10   AAGATAGGGGGGCAACTAAAGGAAGCTCTATTAGATACAGGAGCAGATGATACAGTATTAGAAGAAATGAGTTTG    1946
       LysIleGlyGlyGlnLeuLysGluAlaLeuLeuAspThrGlyAlaAspAspThrValLeuGluGluMetSerLeu

BH10   CCAGGAAGATGGAAACCAAAAATGATAGGGGGAATTGGAGGTTTTATCAAAGTAAGACAGTATGATCAGATACTC    2021
       ProGlyArgTrpLysProLysMetIleGlyGlyIleGlyGlyPheIleLysValArgGlnTyrAspGlnIleLeu

BH10   ATAGAAATCTGTGGACATAAAGCTATAGGTACAGTATTAGTAGGACCTACACCTGTCAACATAATTGGAAGAAAT    2096
       IleGluIleCysGlyHisLysAlaIleGlyThrValLeuValGlyProThrProValAsnIleIleGlyArgAsn
               Aha III
BH10   CTGTTGACTCAGATTGGTTGCACTTTAAATTTTCCCATTAGCCCTATTGAGACTGTACCAGTAAAATTAAAGCCA    2171
       LeuLeuThrGlnIleGlyCysThrLeuAsnPheProIleSerProIleGluThrValProValLysLeuLysPro
         PR ↳ RT
```

Fig. 3A

```
                                    Pol→ ThrGlyArgPheArgThrGlyLysGluAlaProGlnLeuProSerSerAlaGlyAlaAspThrThr
HisIleMetThrAsnCysProAspArgArgGlnAlaGlyPheLeuGlyLeuGlyProTrpGlyLysLysProGlyAsnPheProValAlaGlnValProGlnGlyLeuThrProAlaPro
GACACATCATGACAAACTGCCCAGATAGACAGGCAGGTTTTTAGGACTGGGAAAGAAGCCAGGAAACTTCCCGTGGCCCAAGTCCCCAGGGCTGACACCAACAGCAC
                                                                                                     1900
ProSerGlySerSerSerThrGlyGluIleTyrAlaAlaAlaArgGluThrIleGlnGlySerAspArgGlyLeuThrAlaProArgAlaGly
ProValAspProAlaValAspLeuLeuGluGluLeuLysThrMetGlnGlyGlyLysArgGluGlnArgArgGluGluTyrLysValThrGluValAspLeuHisLeuGluGlnGly
CCCCAGTGGATCCAGCAGTGATCTACTGGAGAATATATGCAGGGAGGAAAGAGAGAGCAAGGAGAGAGGACCAATACAAGGAGGTGACAGAGGTAGACCTGCACCTCGAGCAGG
                                                                                               2000
GlyLysGlnGlyAlaThrAsnArgGlyLeuAlaAlaAlaProGlnPheSerLeuTrpLysArgProValValThrAlaTyrIleGluGlyGlnProValGluValLeuLeuAspThr
           ┌→PR
GluThrProTyrArgGluProThrGluLysTrpGluProLeuLeuHisLeuAsnSerLeuPheGlyLysAspGln
GGGAGACACCATACAGGGAGCCACCAACAGAGGACTTGCTGCACCTCAATTCTCTCTTTGGAAAAGACCAGTAGTCACAGCATACATTGAGGGTCAGCCAGTAGAAGTCTTGTTAGACAC
                                                                                          2100
GlyAlaAspAspSerIleValAlaGlyIleGluLeuGlyAsnAsnTyrSerProLysIleValGlyIleGlyGlyPheIleLysValArgGlnTyrAsnValGluIleGluVal
                                                                             ┌→PR
AGGGGCTGACGACTCAATAGTAGCAGGAATAGAGTTAGGGGAATAACAATCATAAATCCAAGGAATATAATCTACCAGTCGCCAAAGTAGAGCC
                                                                                    2400
LeuAsnLysLysValArgAlaThrIleMetThrGlyAspThrProIleAsnIlePheGlyArgAsnIleLeuThrAlaLeuGlyMetSerLeuAsnLeuProValAlaLeuLysValPro
TCTAAATAAAAAAGGTACGGCCACCATAATGACACAGGCGACACCCCAATCAACATTTTTGGCAGAAATATTCTGACAGCCTTAGGCATGTCATTAAATCTACCAGTCGCCAAAGTAGAGCC
                                                                                      2400
IleLysLysIleMetLeuThrLysAspGlyProLysLeuArgGlnTrpProLeuThrLysGluLysMetGluLysGlyLysGlnLeuLeu
AATAAAAAATAATGCTAACAGGCCAGGGAAGATGGAGAAGGGAAAACTAAGGGCCCCTTAACAAAGAAAAAATAGAGACACTAAAGGAGCT
```

*Fig. 3B*

SUBSTRATE SP-78: ThrThrSerGlnAlaPheProLeuArgAlaGlyNH₂

SP-78

SP-78 + CATHEPSIN D

SP-78 + PR-1

SP-78 + RENIN

SUBSTRATE SP-78:
Thr-Thr-Ser-Gln-Ala-Phe-Pro-Leu-Arg-Ala-Gly-NH₂
PRODUCT 1: Thr-Thr-Ser-Gln-Ala-Phe
PRODUCT 2: Pro-Leu-Arg-Ala-Gly-NH₂
0 hour
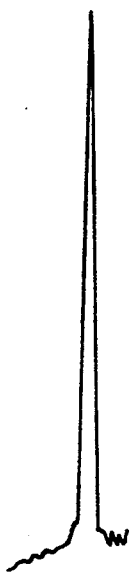
20 hours
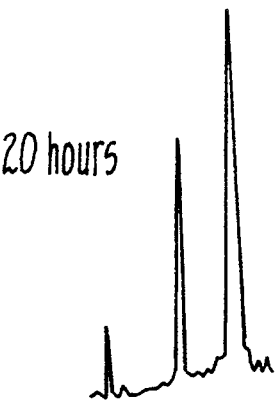
70 hours
2  1  SP-78
*Fig.5*

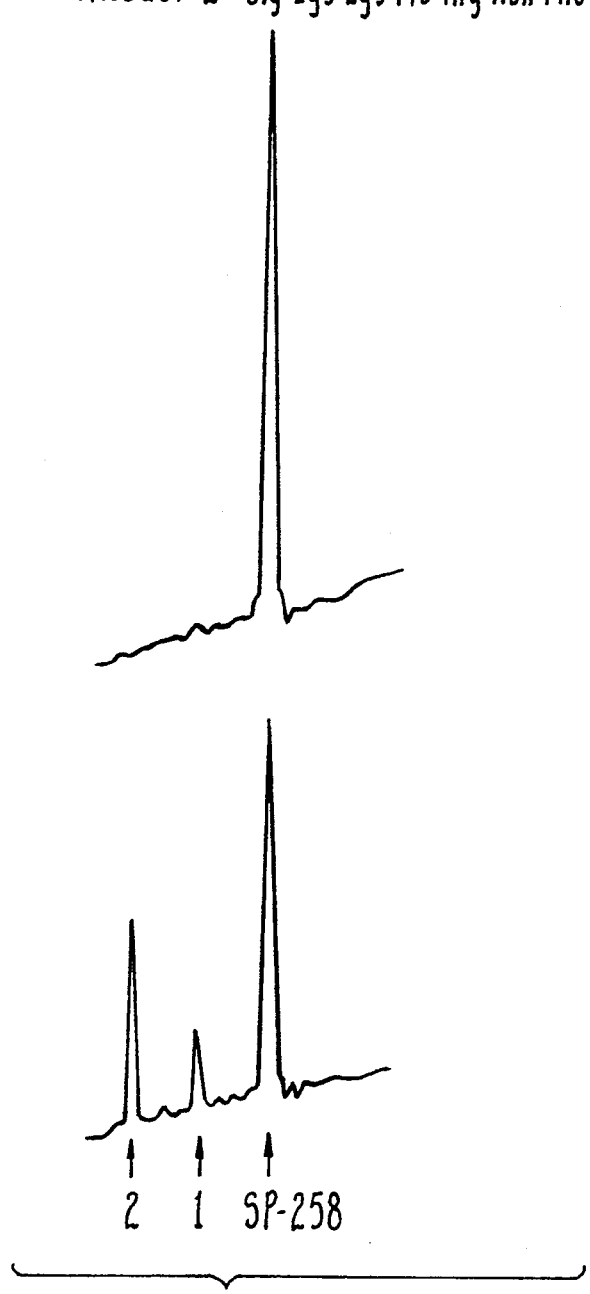
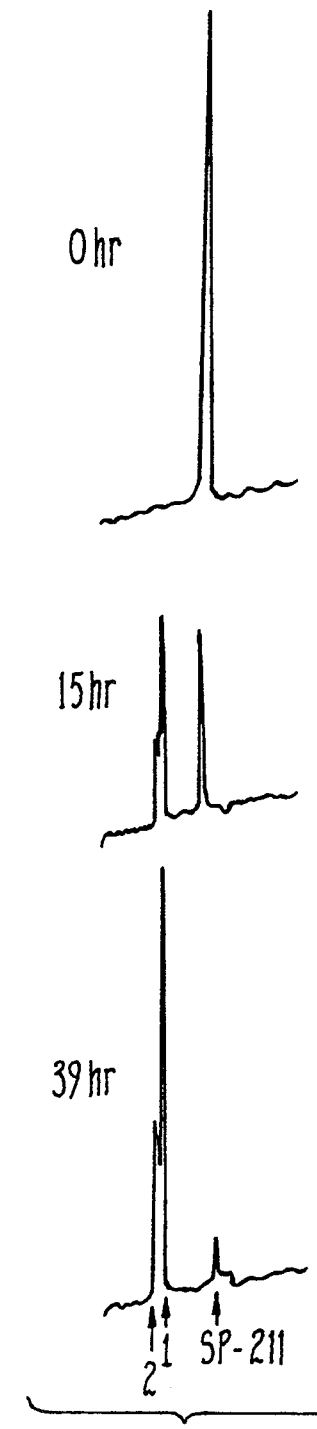
Fig. 6
Fig. 7

HUMAN IMMUNODEFICIENCY VIRUS SPECIFIC PROTEOLYTIC ENZYME AND A METHOD FOR ITS SYNTHESIS AND RENATURATION

This application is a continuation of application Ser. No. 07/201,654, filed Jun. 1, 1988, now abandoned, which is a continuation-in-part of application Ser. No. 07/174,473, filed Mar. 28, 1988, now abandoned, which was a continuation of application Ser. No. 07/107,880, filed Oct. 9, 1987, now abandoned, which in turn was a continuation of application Ser. No. 07/057,183, filed Jun. 1, 1987, now U.S. Pat. No. 5,252,477.

BACKGROUND OF THE INVENTION

We identified and structurally, biochemically and enzymologically characterized human immunodeficiency virus (HIV) protease, as well as its natural polyprotein substrates, in order to develop drugs that inhibit protease activity. It was known from our work on protease deficient MuLV mutants that when precursor polyproteins are not cleaved mature infectious virus can not be produced. Instead, noninfectious particles are made that, however, remain immunogenic because they carry complete envelopes. The idea underlying this research was to ultimately prepare chemical inhibitors that penetrate the infected cell, become incorporated into the budding virus, bind with high affinity to the viral protease or precursor polyproteins, prevent cleavage and lead to the production of non-infectious but still immunogenic viral progeny. The use of these chemical inhibitors would block the spread of HIV infection while allowing for antigenic stimulation of host immunity.

SUMMARY OF THE INVENTION

We have identified the amino acid sequence that constitutes human immunodeficiency virus (HIV) protease, a proteolytic enzyme specific for the virus known as HIV, LAV and HTLV-III, for both HIV-1 and HIV-2 variants. We have also synthesized active protease for both HIV-1 and HIV-2. This enzyme is necessary in the natural synthesis of HIV in the cells of subjects infected by the virus. In the course of natural synthesis it is necessary for protein of the virus to be lysed from precursor proteins. It is this function for which the proteolytic enzyme we have identified and synthesized is specific. Without HIV protease the active virus cannot be reproduced in infected cells and the natural synthesis process will be stopped short of completion. As a result, with our discovery of the structure of this specific protease and our synthesis of the active enzyme, a protease inhibitor specific for this enzyme can be designed. We have produced rabbit antiserum against the C-terminal portion of HIV-1 protease that is specific for HIV-1, which we have used to isolate and characterize natural HIV-1 protease. We have also produced an antibody in rabbits to our synthetic HIV-1 protease, which cross reacts with HIV-2 protease.

BRIEF DESCRIPTION OF THE FIGURES

FIG. 1 illustrates the conservation of amino acid sequences in retroviral proteases, including those of the present invention. The dots represent identical residues or conservative substitutions. The left column identifies the various retroviruses being compared. Retroviral protease target sequences are grouped into classes a, b, c, d, and e. Each class is defined by the amino acids P1, P2, P3, and P4 adjacent the proline target site.

FIG. 2 provides the amino acid sequence for HIV-1 (BH10) protease, and the non-homologous sequences found for HIV-2 protease.

FIG. 3 provides DNA and amino acid sequences for HIV, including the complete sequence for HIV-1 protease (FIG. 3a) and HIV-2 protease (FIG. 3b).

FIGS. 5, 6 and 7 illustrate proteolytic cleavage of the Phe-Pro bond in SP-78, Sp-258, and SP-211 substrates by HIV-2 protease.

DESCRIPTION OF THE PREFERRED EMBODIMENTS

Figure 4A:
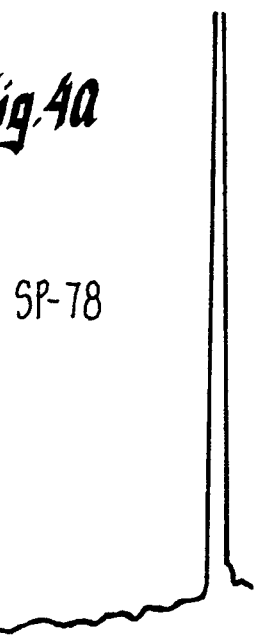
FIGS. 4a–4d illustrates the proteolytic cleavage of HIV substrates with the presently synthesized HIV-1 protease, demonstrating activity.
Figure 4C:
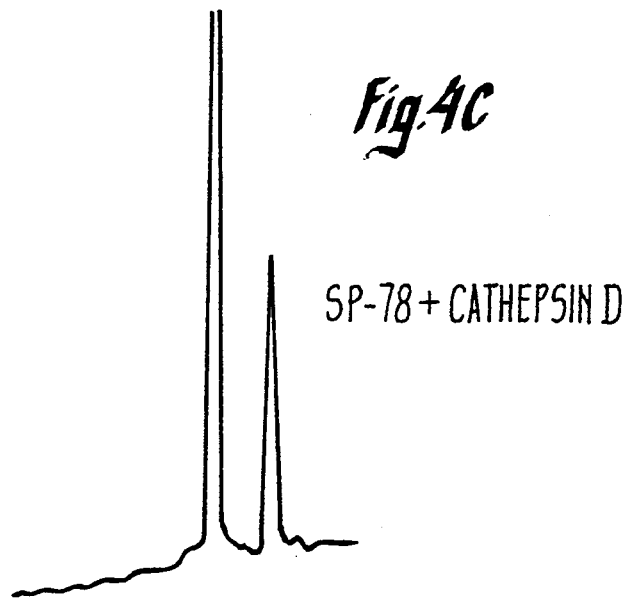

The entire DNA sequence coding for HIV was known. However, the portions of that sequence coding for particular active peptides and proteins, such as the protease, had not been determined prior to this invention. As we had previously identified proteases specific for human retroviruses, and we had identified homologies in the sequences coding for proteases necessary in the natural synthesis of these other retroviruses, we were able to identify sections in the DNA sequence coding for HIV proteins that should be within the sequence coding for a protease specific for HIV and necessary for its natural synthesis. (Copeland and Oroszlan, "A Synthetic Dodecapeptide Substrate For Type C RNA Tumor Virus Associated Proteolytic Enzyme," *PEPTIDES: Synthesis-Structure-Function,* Pierce Chemical Company, 1981, and Yoshinaka et al, "Murine Leukemia Virus Protease Is Encoded By The gag-pol Gene and Is Synthesized Through Suppression of an Amber Termination Codon", *Proc. Natl. Acad. Sci., USA,* Vol. 82, pages 1618–1622, March 1985, included herein in their entirety by reference). Our previous work indicated to us that certain sequences were conserved in retroviral proteases; these are set forth in FIG. 1.

HIV protease is a 99 amino acid peptide, which has a molecular weight of 11K–11.5K daltons measured by SDS PAGE. The amino acid sequence is given in FIG. 2, as marked, beginning with ProGlnIle . . . The complete amino acid sequence given is for HIV-1$_{BH10}$. In the second row in FIG. 2, the amino acids for HIV-2 are given where they differ from those in HIV-1. FIG. 3a indicates the position of the 99 amino acid peptide in the HIV-1 sequence. The peptide sequence is shown in the bottom line in each grouping. The first line in each grouping is the DNA sequence coding for the HIV-1 protease. The second line in the first grouping is an alternative amino acid sequence, which is correct for the expression of certain portions of HIV-1 protein. However, due to a reading frame shift prior to the protease, the sequence we have identified in the third line and repeated in FIG. 2, is the actual amino acid sequence of HIV-1 protease.

After identifying the amino acid sequence for HIV protease, we synthesized the C-terminal peptide consisting of 15 amino acids (IleGlyArgAsnLeuLeuThrGlnIleGlyCysThrLeuAsn Phe). With this 15 amino acid synthetic peptide we generated a rabbit antiserum. The rabbit antiserum was then used to detect natural protease from HIV. It also was used to identify the protease fraction after HPLC separation. The N terminal of the HPLC purified protease was then sequenced by Edmond degradation. We could then determine that the N terminal began with the Pro located 99 amino acids upstream from the previously identified N terminal Pro beginning the reverse transcriptase sequence, shown at RT in FIG. 3a.

Having determined that the sequence we identified was for HIV protease, we proceeded by solid phase synthesis using the Merrifield method to synthesize the 99 amino acid peptide (Merrifield R. B. (1963), "Solid Phase Peptide Synthesis I". *J. Amer. Chem. Soc.* 85, 2149–2154, included herein by reference). The synthesis was done using the semiautomatic synthesis procedures with an Applied Biosystems program and an Applied Biosystems 430 Peptide synthesizer (Foster City, Calif.).

The 99 amino acid polypeptide synthesized having the sequence shown in FIG. 2 and FIG. 3A is based on the DNA sequence of HIV-1$_{BH10}$ (Ratner, L. et al, (1985) "Complete Nucleotide sequence of the AIDS Virus, HTLV-III.", NATURE, 313, 277–284, included herein by reference). This synthetic protease is designated here as PR-1.

In addition we have synthesized another HIV protease designated PR-2, which corresponds to the sequence of another HIV strain (HIV-2$_{ROD}$) as reported by Guyader, M. et al, (1987) "Genome Organization and Transactivation of the Human Immunodeficiency Virus Type 2." NATURE, 326, 662–669. The variation in amino acid sequence between PR-1 and PR-2 is indicated in FIG. 2. The complete sequence of PR-2 is given in FIG. 3b. The sequences of PR-1 and PR-2 are both comprised of 99 amino acids and share 47 identical residues in their sequence, and an overall homology of approximately 76%. The putative active site sequences of PR-1 and PR-2 are identical (see identical residues 23 to 30, Leu Leu Asp Thr Gly Ala Asp Asp, aligned in FIG. 2) and the natural cleavage sites in the two strains of HIV are very similar as determined in our laboratory (Henderson, L. E. et al, (1988) "Analysis of Proteins and Peptides Purified From Sucrose Gradient Banded HTLV-III." in Human Retroviruses, Cancer and AIDS: Approaches to Prevention and Therapy, pp. 135–147, Alan R. Liss Inc.; Henderson L. E. et al, (1988) "Molecular Characterization of gag Proteins From Simian Immunodeficiency Virus Siv$_{mne}$. J. Virol, In Press").

EXAMPLE I

Synthesis

The 99 amino acid (99 met) residue proteases, PR-1 and PR-2, were assembled by the solid phase method in an Applied Biosystems Model 430A peptide synthesizer. The resin and protected amino acids were purchased from Applied Biosystems. Side chain protecting groups were benzyl (Bzl) for aspartic acid, glutamic acid, serine and threonine; 4-methylbenzyl for cysteine; tosyl for arginine and histidine; 2-chlorobenzyl- oxycarbonyl for lysine; 2-bromobenzyloxycarbonyl for tyrosine; and formyl for tryptophan. The tert-butoxycarbonyl (Boc) group protected the a-amino group. The synthesis began with the Boc-carboxyl amino acid substituted on a phenylacetamindemethyl resin. The instrument program converted the amino acids to the symmetric anhydrides just prior to the coupling step. Arginine, asparagine and glutamine were double coupled using 1-hydroxybenzotriazole. Following completion of all the coupling steps, the peptide-resin was dried in a desiccator. 0.3 g was then reacted with 0.75 ml p-cresol, 0.25 ml p-thiocresol, 6.5 ml dimethyl-sulfide and 2.5 ml hydrogen fluoride in an all-teflon apparatus with magnetic stirring for 2 hours at 0° C., solvents were then removed by vacuum, the mixture extracted with ether and dried with nitrogen. The second step of deprotection proceeded with 0.6 ml p-cresol and 9 ml hydrogen fluoride for one hour. Solvents again were removed with vacuum, the mixture filtered, washed with ether and dried with nitrogen.

Peptides of various length, corresponding to the natural cleavage sites that occur in retroviral gag polyproteins, were synthesized and purified according to published methods (Copeland and Oroszlan (Supra),and Copeland, T. D. et al, "Envelope Proteins of Human T Cell Leukemia Virus Type I: Characterization by Antisera to Synthetic Peptides and Identification of a Natural Epitope,": *The Journal of Immunology*, Vol 137, 2945–2951, No 9, Nov. 1, 1986.)

As synthesized, the peptide is linear and demonstrates no activity as a proteolytic enzyme. In addition to removing blocking groups, therefore, it was necessary to convert the protease to its natural stereospecific conformation in order to exhibit proteolytic activity. As produced, the synthetic HIV protease was extracted in a strong acid. It was necessary, thereafter, to submit it to treatment and purification using specific buffer systems and dialysis. Thereafter, we proceeded by trial and error to effect renaturation and to refold the peptide into its natural stereospecific confirmation. This was done through recovery in guanidine hydrochloride solution, concentration, removal of all solutes and recovery in an aqueous solution. The proper folding was accomplished through a series of trial and error steps. The correct folding of the peptide is the result of intra and intermolecular forces and bonding, and of the characteristics of the media to which we subjected the synthetic protein.

Purification and Renaturation of Synthetic Protease 25 mg of the resin plus Peptide mixture, including synthetic 99 amino acid protease, were extracted into 6M Gnd-HCl dissolved in Tris-HCL at pH 8.0. The PR-1 solution also contained the reducing agent, dithiothreitol (DTT). In the purification procedure for PR-2, DTT was not used. Desalting partial purification was accomplished by gel permeation chromatograpy on G-25 Sephadex (Pharmacia). Fractions of the excluded peak were collected and subjected first to slow dialysis in Tris-HCl buffer at 4° C. The fractions were then dialyzed against several changes of Pipes buffer at pH 7.0 containing NP-40, with or without DTT, (Hafenrichter, R. & Thiel, H. J., "Simian Sarcoma Virus-Encoded gag-Related Protein: In Vitro Cleavage by Friend Leukemia Virus-Associated Proteolytic Activity" *Virology*, 143, 143–152 (1985)).

Antibody was also prepared to the synthetic PR-1 99 amino acid protease 1 mg of the crude peptide was mixed with phosphate buffered saline and Freund's complete adjuvant and then administered to a New Zealand white rabbit at several sites subcutaneously on the back. At two week intervals, boosts were made with 0.1 mg in Freund's incomplete adjuvant. After one month the animal was bled at two week intervals. Positive antisera to the PR-1 99 mer was obtained. This antibody was cross reactive with PR-2.

We were able to obtain a synthetic protein that showed specific proteolytic activity for HIV. Assays to confirm that we had produced the active protein were conducted by incubating the synthetic protease with natural vital substrates and with synthetic vital substrates. The results demonstrated that our synthetic HIV protease was specific for the characteristic cleavage sites. The assay methods employing synthetic substrates used were essentially as described in Copeland and Oroszlan (Supra).

EXAMPLE II

Protease Assays

Synthetic peptides corresponding to cleavage sites in various gag precursors were incubated with PR-1 or PR-2 in various buffered solutions at various pHs and aliquots removed at various time points. To analyze for cleavage of the substrates, 50 microliters of saturated Gnd-HCl was added and TFA added to lower the pH to 2. The contents were then applied to a $\mu$ Bondapak C18 column (Waters) and subjected to a 30 minute 0 to 40% $CH_3CN$ containing 0.05% TFA gradient. Between each chromatographic assay the column was washed with 60% $CH_3CN$. Following hydrolysis in vacuo at 110 degrees with 6N HCl for 20 hours peaks were collected manually and analyzed for amino acid composition. Amino acid analysis was performed on a Waters Pico-Tag TM system.

This activity is illustrated in FIG. 4. FIG. 4a illustrates MuLV synthetic peptide containing the known proteolytic cleavage site. FIG. 4b shows the same peptide after being incubated with our synthetic HIV protease PR-1. Two of the peaks to the left of the main peptide indicate products of cleavage of the MuLV substrate. FIGS. 4c and 4d illustrate cleavage of the same substrate using two other proteases, cathepsin D and renin, respectively. As can be seen from the products to the right of the substrate peak, those enzymes cleave the substrate at different cleavage sites.

EXAMPLE III

Figure 4B:
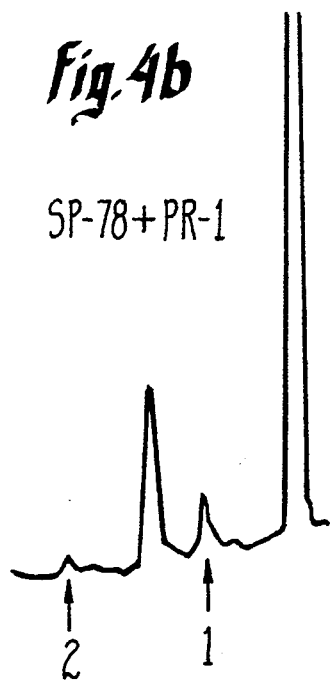
Figure 4D:
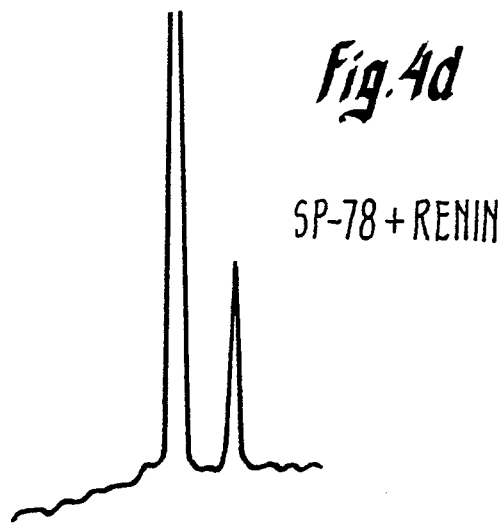

Cleavage of synthetic peptide SP-78 that corresponds to an undecopeptide sequence present at the Phe-Pro cleavage site in murine leukemia virus gag polyprotein is shown in FIG. 5. To an appropriate amount of lyophilized SP-78 was added the synthetic 99 amino acid PR-2 (approximately 100 ng) in the stock solution containing NP-40. The pH was adjusted to 6.5 with sodium phosphate buffer in a total volume of 25 $\mu$l. The reaction mixture contained a final concentration of approximately 0.2 m sodium phosphate, 0.35% NP-40 and 10% glycerol. The solution was incubated at room temperature and aliquots were removed immediately after mixing (0 hr), after 20 hrs, and after 70 hrs of incubation. Substrate and products were separated and recovered by HPLC. The chromatographic profiles illustrated in FIG. 5 show the substrate and cleavage products 1 and 2 with their specific sequences. The sequences were confirmed by amino acid analyses of the peak fractions. These results provided evidence that the Phe-Pro bond was cleaved in a specific fashion, the same as accomplished by the viral protease under natural conditions. A Progression with time of the enzymatic cleavage is documented. The elution time, a well defined parameter dependent on peptide composition, is the same for products 1 and 2, as shown in FIG. 4b; where the same substrate was cleaved by PR-1. Note that the extent of cleavage as demonstrated by the two smaller peaks to the left of the substrate peak was much smaller due to the less favorable experimental conditions used in the initial experiments with PR-1.

The cleavage of synthetic peptide corresponding to a Phe-Pro site sequence in the HIV-2 gag polyprotein, SP-258 is shown in FIG. 6. Results are shown for a single time point in incubation, but subsequent amino acid analysis provided convincing evidence that the cleavage of a single bond occurred at the expected site. See sequence of substrate and products in FIG. 6. The substrate and enzyme (approximately 120 ng) were incubated in low molarity Pipes buffer pH 7.0 containing NP-40, at room temperature. DTT is not required for cleavage of cysteine free substrates with PR-2 since this enzyme does not contain any cysteine in its structure.

The cleavage of synthetic peptide SP-211, corresponding to a TYR-PRO cleavage site sequence in HIV-1 gag polyprotein, is shown in FIG. 7, as obtained at 15 and 39 hrs of incubation at room temperature. Approximately 100 ng of PR-2 was used as in the previous experiment, but the ionic strength was higher. The buffer was 0.2M sodium phosphate, pH 6.5, and contained in addition 15 mM sodium chloride, 5% glycerol and 0.2% NP-40. Incubation was again at room temperature. Product #2, tetrapeptide PRO-ILE-VAL GLN amide, as expected, elutes before product #1, a pentapeptide with the sequence VAL-Ser-Gln-Asn-Tyr.

We claim:

1. Essentially pure HIV-2 protease, a proteolytic enzyme necessary for cleaving precursor polyproteins of HIV-2.

2. The proteolytic enzyme of claim 1, comprising the amino acid sequence:

ProGlnPheSerLeuTypLysArgProValValThrAlaTyrIleGluGlyGlnProVal
GluValLeuLeuAspThrGlyAlaAspAspSerIleValAlaGlyIleGluLeuGlyAsn
AsnTyrSerProLysIleValGlyGlyIleGlyGlyPheIleAsnThrLysGluTyr
LysAsnValGluIleGluValLeuAsnLysLysValArgAlaThrIleMetThrGlyAsp
ThrProIleAsnIlePheGlyArgAsnIleLeuThrAlaLeuGlyMetSerLeuAsnLeu.

3. The proteolytic enzyme of claim 2 prepared by chemical synthesis in a stereospecific conformation that provides proteolytic activity.

* * * * *